United States Patent
Nakao et al.

(10) Patent No.: US 11,911,742 B2
(45) Date of Patent: Feb. 27, 2024

(54) HYDROCARBON ADSORBENT

(71) Applicant: TOSOH CORPORATION, Yamaguchi (JP)

(72) Inventors: Keita Nakao, Yamaguchi (JP); Ryo Mitsuhashi, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

(21) Appl. No.: 18/130,577

(22) Filed: Apr. 4, 2023

(65) Prior Publication Data

US 2023/0234022 A1    Jul. 27, 2023

Related U.S. Application Data

(63) Continuation of application No. 16/976,642, filed as application No. PCT/JP2019/008049 on Mar. 1, 2019, now Pat. No. 11,648,527.

(30) Foreign Application Priority Data

Mar. 2, 2018   (JP) ................................ 2018-037603

(51) Int. Cl.
| | |
|---|---|
| *B01J 20/18* | (2006.01) |
| *B01D 53/04* | (2006.01) |
| *B01D 53/94* | (2006.01) |
| *B01J 20/28* | (2006.01) |
| *C01B 39/20* | (2006.01) |
| *C07C 7/12* | (2006.01) |
| *F01N 3/08* | (2006.01) |
| *F01N 3/28* | (2006.01) |

(52) U.S. Cl.
CPC .............. *B01J 20/18* (2013.01); *B01D 53/04* (2013.01); *B01D 53/9486* (2013.01); *B01J 20/28009* (2013.01); *C01B 39/20* (2013.01); *C07C 7/12* (2013.01); *F01N 3/0814* (2013.01); *F01N 3/0835* (2013.01); *F01N 3/2803* (2013.01); *B01D 2253/108* (2013.01); *B01D 2257/702* (2013.01); *C01P 2002/60* (2013.01); *C01P 2002/78* (2013.01); *C01P 2006/42* (2013.01); *F01N 2330/02* (2013.01); *F01N 2330/32* (2013.01); *F01N 2370/04* (2013.01); *F01N 2570/12* (2013.01)

(58) Field of Classification Search
None
See application file for complete search history.

(56) References Cited

U.S. PATENT DOCUMENTS

| | | | |
|---|---|---|---|
| 3,649,176 A | 3/1972 | Rosback | |
| 3,649,177 A | 3/1972 | Rosback | |
| 4,264,562 A | 4/1981 | Kostinko | |
| 4,376,106 A | 3/1983 | Miyanohara | |
| 4,717,398 A | 1/1988 | Pearce | |
| 4,985,210 A | 1/1991 | Minami | |
| 6,215,037 B1 | 4/2001 | Padin et al. | |
| 2001/0008624 A1 | 7/2001 | Takahashi | |
| 2007/0004591 A1 | 1/2007 | Itabashi et al. | |
| 2015/0265975 A1* | 9/2015 | Liu ..................... | B22F 5/006 427/244 |
| 2019/0248661 A1 | 8/2019 | Dodin | |
| 2020/0223770 A1 | 7/2020 | Laroche | |
| 2020/0406226 A1* | 12/2020 | Nakao ................... | B01J 20/186 |

FOREIGN PATENT DOCUMENTS

| | | |
|---|---|---|
| CN | 107262145 A | 10/2017 |
| JP | 48-3757 B | 2/1973 |
| JP | 48-102800 A | 12/1973 |
| JP | 60-179135 A | 9/1985 |
| JP | 2-75327 A | 3/1990 |
| JP | 05-813 A | 1/1993 |
| JP | 6-126165 A | 5/1994 |
| JP | 6-210163 A | 8/1994 |
| JP | 6-210164 A | 8/1994 |
| JP | 7-96178 A | 4/1995 |
| JP | 7-213910 A | 8/1995 |
| JP | 8-229387 A | 9/1996 |
| JP | 2002-528427 A | 9/2002 |
| JP | 2005-230797 A | 9/2005 |

OTHER PUBLICATIONS

International Search Report issued in International Patent Application No. PCT/JP2019/008049, dated Jun. 4, 2019, and English Translation thereof.
International Preliminary Report on Patentability issued in International Patent Application No. PCT/JP2019/008049, dated Jun. 4, 2019, and English Translation thereof.
Extended European Search Report issued in corresponding European Paten Application No. 19759904.6 dated Oct. 25, 2021.
Tsutsumi et al. "Cumene Cracking Activity of Zeolite Catalysts III. Effect of Copper(II) Ion Exchange on the Faujasite_Type Synthetic Zeolites", Journal of Catalysis, vol. 24, No. 1 Jan. 1, 1972, pp. 1-7, XP055851560, US ISSN: 0021-9517, DOI: 10.1016/0021-9517(72)90002-4.
"FAU: Framework Type", Datatbase of Zeolite Structures, Jul. 1, 2007), p. 1, XP055851565, URL:https://europe.iza-structure.org/IZA-SC/framework.php?STC=FAU (retrieved on Oct. 14, 2021).

* cited by examiner

*Primary Examiner* — Tam M Nguyen
(74) *Attorney, Agent, or Firm* — GREENBLUM & BERNSTEIN, P.L.C.

(57) ABSTRACT

A hydrocarbon adsorbent having high hydrocarbon adsorbing properties even after exposed to a high temperature/high humidity reducing atmosphere, includes a FAU type zeolite having in ESR measurement a spin concentration of at least $1.0 \times 10^{19}$ (spins/g) and a ratio of a peak intensity at a magnetic field of at least 260 mT and at most 270 mT to a peak intensity at a magnetic field of at least 300 mT and at most 320 mT of at least 0.25 and at most 0.50 Å and containing bivalent copper. The hydrocarbon adsorbent may be used for a method for adsorbing hydrocarbons to be exposed to a high temperature/high humidity environment, and may be used particularly for a method for adsorbing hydrocarbons in an exhaust gas of an internal combustion engine, such as an automobile exhaust gas.

6 Claims, 3 Drawing Sheets

HYDROCARBON ADSORBENT

CROSS REFERENCE TO RELATED APPLICATIONS

This is a Continuation of U.S. application Ser. No. 16/976,642, which is a US National Stage entry of PCT/JP2019/008049, filed Mar. 1, 2019, which claims priority to JP App. No. 2018-037603, filed Mar. 2, 2018. The disclosure of each of the above-identified documents is incorporated herein by reference in its entirety.

TECHNICAL FIELD

An exhaust gas discharged from an internal combustion engine used for vehicles such as automobiles and ships contains a large quantity of hydrocarbons, and the hydrocarbons discharged from the internal combustion engine are clarified by a three way catalyst. However, the three way catalyst requires a temperature environment of at least 200° C. to function, and in a temperature range in which the three way catalyst does not function, for example, at the time of cold start, the hydrocarbons are adsorbed in a hydrocarbon adsorbent, discharged from the adsorbent at a temperature range at which the three way catalyst starts functioning, and decomposed and clarified by the three way catalyst.

The temperature of an automobile exhaust gas reaches 900° C. or higher depending upon the engine operation state. Further, the exhaust gas composition varies depending upon the operation state. The air fuel ratio (air/fuel mixture) when oxygen and a fuel mixture in the mixed gas react with each other without any excess nor deficiency is called theoretical air fuel ratio. In actual operation, the fuel does not always burn at the theoretical air fuel ratio, and lean burn with an air fuel ratio higher than the theoretical air fuel ratio and rich burn with an air fuel ratio lower than the theoretical air fuel ratio are employed depending upon the load state. The lean burn is burning at an oxygen concentration higher than that of complete combustion of the fuel mixture, and the exhaust gas contains oxygen in an amount of from 3 to 15 vol %, that is, in an oxidizing atmosphere. On the other hand, rich burn is combustion with excess fuel, and the exhaust gas contains unburned hydrocarbons and is thereby in a reducing atmosphere. Accordingly, the hydrocarbon adsorbent is required to have high thermal durability in oxidizing/reducing atmosphere.

As a method for adsorbing and clarifying hydrocarbons from an exhaust gas at low temperature, an adsorbing catalyst for purifying exhaust gas comprising zeolite with a $SiO_2/Al_2O_3$ molar ratio of from 50 to 2,000, such as mordenite, β-zeolite or ZSM-5 and containing at least one selected from the group consisting of Pt, Pd and Rh (Patent Document 1), a molecular sieve having Ag supported (Patent Document 2) and ZSM-5 zeolite comprising Cu ion-exchanged with at least one metal selected from the group consisting of Co, Ni, Cr, Fe, Mn, Ag, Au, Pt, Pd, Ru, Rh and V (Patent Document 3) have been proposed.

Each of methods for adsorbing and removing hydrocarbons using such adsorbents employs a system such that hydrocarbons contained in an exhaust gas are once adsorbed in the adsorbent at a low temperature region at the time of start of the engine, and the hydrocarbons desorbed from the adsorbent at a temperature at which the exhaust gas clarifying catalyst functions or higher, are clarified by a catalyst, and each of the conventional adsorbents is insufficient in durability in a hot and humid environment particularly in durability at high temperature of about 900° C.

PRIOR ART DOCUMENTS

Patent Documents

Patent Document 1: JP-A-H07-213910
Patent Document 2: JP-A-H06-126165
Patent Document 3: JP-A-H06-210163

DISCLOSURE OF INVENTION

Technical Problem

It is an object of the present invention to provide a hydrocarbon adsorbent having high hydrocarbon adsorbing properties even after exposed to a high temperature/high humidity reducing atmosphere.

Solution to Problem

The present inventors have conducted extensive studies on hydrocarbon adsorbents used to adsorb hydrocarbons mainly in an exhaust gas of an internal combustion engine and their properties. As a result, they have found a hydrocarbon adsorbent having high hydrocarbon adsorbing properties even after exposed to a high temperature/high humidity reducing atmosphere by controlling physical properties of a FAU structure zeolite.

That is, the present invention provides the following.
[1] A hydrocarbon adsorbent which comprises a FAU type zeolite having a lattice constant of at least 24.29 Å and containing copper.
[2] The hydrocarbon adsorbent according to [1], wherein the FAU type zeolite has an average crystal size of at least 0.45 μm.
[3] The hydrocarbon adsorbent according to [1] or [2], wherein the FAU type zeolite has a copper content of at least 0.5 wt % and at most 4.0 wt %.
[4] The hydrocarbon adsorbent according to any one of [1] to [3], wherein the FAU type zeolite has an alkali metal content as calculated as oxides of at most 1 wt %.
[5] The hydrocarbon adsorbent according to any one of [1] to [4], wherein the FAU type zeolite has a hydrogen consumption peak with a peak top at a temperature of at least 300° C. and at most 500° C., in $H_2$-TRP measurement in a state after subjected to exposure treatment to a reducing atmosphere at a temperature of at least 800° C. and at most 1,000° C. and then to exposure treatment to an oxidizing atmosphere at a temperature of at least 400° C. and at most 600° C.
[6] The hydrocarbon adsorbent according to any one of [1] to [5], wherein the FAU type zeolite has, in ESR measurement, a spin concentration of a least $1.0 \times 10^{19}$ (spins/g) and a ratio of a peak intensity at a magnetic field of at least 260 mT and at most 270 mT to a peak intensity at a magnetic field of at least 300 mT and at most 320 mT of at least 0.25 and at most 0.50.
[7] A method for treating a hydrocarbon-containing gas, which uses the hydrocarbon adsorbent as defined in any one of [1] to [6].

Advantageous Effects of Invention

According to the present invention, it is possible to provide a hydrocarbon adsorbent having high hydrocarbon adsorbing properties even after exposed to a high temperature/high humidity reducing atmosphere.

DESCRIPTION OF EMBODIMENTS

Figure 1:
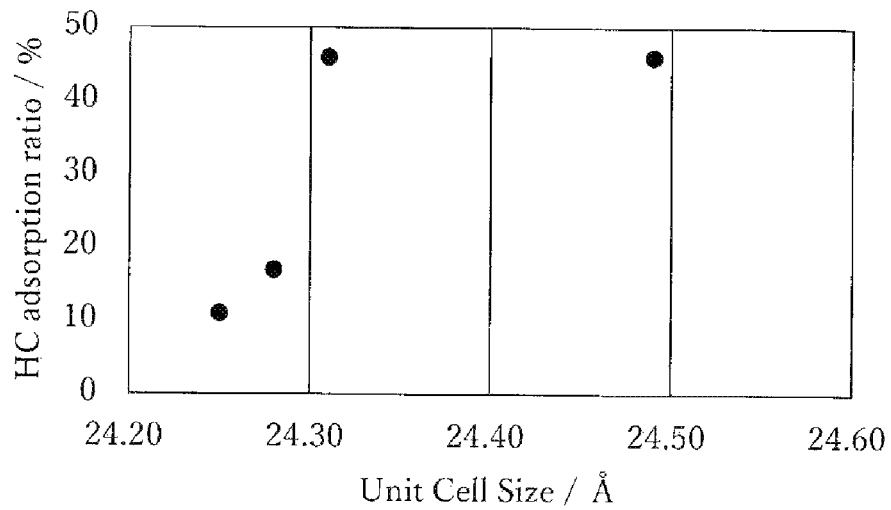
FIG. 1 is a graph illustrating the relation between the lattice constant and the hydrocarbon adsorption ratio after reduction hydrothermal durability treatment.

Now, embodiments of the hydrocarbon adsorbent of the present invention will be described.

In an embodiment of the present invention, the hydrocarbon adsorbent contains a FAU type zeolite. The FAU type zeolite is a zeolite having a FAU structure, and is preferably a crystalline aluminosilicate having a FAU structure. The FAU structure is framework type code defined as "FAU" by the International Zeolite Association (hereinafter sometimes referred to simply as "framework type code"). The structure may be confirmed by a powder X-ray diffraction (hereinafter sometimes referred to as "XRD") pattern as described in Collection of simulated XRD powder patterns for zeolites, Fifth revised edition (2007).

The crystal structure of the FAU type zeolite comprises structural units of sodalite cages consisting of 4-oxygen rings and 6-oxygen rings, and double six-oxygen rings (hereinafter sometimes referred to as "D6R"), and has pores formed of 12-oxygen rings (hereinafter sometimes referred to as "12-oxygen ring pores") formed of such structural units three-dimensionally bonded. By the FAU type zeolite having the 12-oxygen ring pores, it can adsorb even bulky hydrocarbons such as aromatic hydrocarbons. Further, copper and aluminum constituting the structural units have strong interaction. In the FAU type zeolite, aluminum constituting D6R and copper strongly interact with each other, whereby copper is held in zeolite, mainly in the crystal structure, with a homogeneously dispersed state, and the hydrocarbon adsorbing properties of the FAU type zeolite will hardly decrease.

In the embodiment of the present invention, the FAU type zeolite has a lattice constant of at least 24.29 Å, preferably at least 24.30 Å. In a FAU type zeolite having a lattice constant of less than 24.29 Å, although it has D6R in its crystal structure, the interaction between copper and aluminum constituting the framework of the crystal structure is weak. As a result, aggregation of copper by exposure to a high temperature/high humidity reducing atmosphere is likely to proceed. As a result, the hydrocarbon adsorbing properties will remarkably decrease after exposure to a high temperature/high humidity reducing atmosphere. With a view to improving thermal stability of the FAU structure, the lattice constant is preferably at most 24.55 Å, more preferably at most 24.51 Å, further preferably at most 24.50 Å, particularly preferably at most 24.48 Å. In one embodiment, the lattice constant is preferably at least 24.40 Å and at most 24.50 Å, more preferably at least 24.45 Å and at most 24.50 Å.

In the embodiment of the present invention, the lattice constant is a value measured by the method for measuring the lattice constant of the FAU type zeolite in accordance with ASTM D3942-80.

In the embodiment of the present invention, so long as the FAU type zeolite has the above lattice constant, the molar ratio of silica to alumina (hereinafter sometimes referred to as "$SiO_2/Al_2O_3$ ratio") is optional. Usually, the $SiO_2/Al_2O_3$ ratio and the lattice constant of zeolite have a direct correlation with each other. On the other hand, in the embodiment of the present invention, the $SiO_2/Al_2O_3$ ratio and the lattice constant of the FAU type zeolite have no direct correlation. In the embodiment of the present invention, the $SiO_2/Al_2O_3$ ratio of the FAU type zeolite may be at least 1.25 and at most and is preferably at least 3.0 and at most 30.0. As a particularly preferred $SiO_2/Al_2O_3$ ratio, at least 3.0 and at most 25.0 may be mentioned, at least 4.0 and at most 12.0 is preferred, at least 4.5 and at most 9.5 is more preferred.

In the embodiment of the present invention, the FAU type zeolite contains copper. As compared with a FAU type zeolite containing copper (hereinafter sometimes referred to as "copper-containing FAU type zeolite"), a FAU type zeolite containing no copper has a remarkably low hydrocarbon holding power. Most of the hydrocarbons adsorbed in the FAU type zeolite containing no copper are readily discharged from the FAU type zeolite. When the FAU type zeolite contains copper, the interaction between the hydrocarbons and the FAU type zeolite will be stronger, and the adsorbed hydrocarbons will hardly be discharged from the FAU type zeolite containing copper.

In the embodiment of the present invention, the state of copper contained in the FAU type zeolite is preferably bivalent copper ($Cu^{2+}$), more preferably homogeneously dispersed bivalent copper (hereinafter sometimes referred to as "dispersed copper"). The dispersed copper may be at least either one of $Cu^{2+}$ ion and CuO cluster, and is preferably $Cu^{2+}$ ion.

In the embodiment of the present invention, the state of copper contained in the FAU type zeolite may be confirmed by a hydrogen consumption peak accompanying reduction of copper, in $H_2$-TPR measurement. In the $H_2$-TPR measurement, the bivalent copper is confirmed by a hydrogen consumption peak (hereinafter sometimes referred to as "bivalent copper peak") with a peak top at a temperature of higher than 200° C. and at most 500° C. Further, the dispersed copper such as $Cu^{2+}$ ion is confirmed by a hydrogen consumption peak (hereinafter sometimes referred to as "dispersed copper peak") with a peak top at a temperature of at least 300° C. and at most 500° C., and agglomerated bivalent copper, such as copper oxide (CuO) (hereinafter sometimes referred to as "agglomerated copper") is confirmed by a hydrogen consumption peak (hereinafter sometimes referred to as "aggregated copper peak") with a peak top at a temperature of higher than 200° C. and lower than 300° C. Further, monovalent copper is confirmed by a hydrogen consumption peak with a peak top at a temperature of higher than 500° C.

In the embodiment of the present invention, as the conditions for $H_2$-TPR measurement, the following conditions may be mentioned.

| | |
|---|---|
| Measurement atmosphere: | 5 vol % hydrogen-containing helium atmosphere |
| Flow rate: | 30 mL/min |
| Temperature-raising rate: | 10° C./min |
| Measurement temperature: | 50 to 700° C. |
| Sample amount: | 0.3 g |

In the embodiment of the present invention, the FAU type zeolite preferably has dispersed copper even after exposed to a high temperature reducing atmosphere and then exposed to a high temperature oxidizing atmosphere, more preferably has a dispersed copper peak in $H_2$-TPR measurement in a state after subjected to exposure treatment to a reducing atmosphere at a temperature of at least 800° C. and at most 1,000° C. and then to exposure treatment to an oxidizing atmosphere at a temperature of at least 400° C. and at most 600° C. Particularly, the FAU type zeolite preferably has a dispersed copper peak in $H_2$-TPR measurement after subjected to exposure treatment to a high temperature reducing atmosphere (hereinafter sometimes referred to as "high temperature reducing treatment") and then to an exposure treatment to a high temperature oxidizing atmosphere (hereinafter sometimes referred to as "high temperature oxidizing treatment").

| | |
|---|---|
| High temperature reduction treatment: | |
| treatment atmosphere: | 5 vol % hydrogen-containing helium flowing atmosphere |
| flow rate: | 30 to 100 mL/min |
| treatment temperature: | at least 850° C. and at most 950° C. |
| treatment time: | at least 10 minutes and at most 1 hour |
| sample amount: | 0.2 to 0.4 g |
| High temperature oxidizing treatment: | |
| treatment atmosphere: | air atmosphere |
| treatment temperature: | at least 450° C. and at most 550° C. |
| treatment time: | at least 30 minutes and at most 2 hours |
| sample amount: | 0.2 to 0.4 g |

Presence of the dispersed copper peak after the high temperature reducing treatment and the high temperature oxidizing treatment indicates copper being contained in the FAU type zeolite in a highly dispersed state even after such high temperature treatments.

In the embodiment of the present invention, the state of copper contained in the FAU type zeolite may also be confirmed by an ESR spectrum. For example, as the method for measuring the ESR spectrum, the following conditions may be mentioned.

| | |
|---|---|
| Microwave frequency: | 9.2 to 9.5 GHZ |
| Measurement range: | 0 to 1,000 mT |
| Sweep magnetic field width: | ±500 mT |
| Magnetic field modulation: | 90 to 110 KHz |
| Response: | 0.05 to 0.5 sec. |
| Magnetic field sweep time: | 1 to 10 min. |
| Microwave output: | 0.1 to 5 mW |
| Pretreatment temperature: | 300 to 500° C. |
| Pretreatment time: | 30 minutes to 5 hours |

The double integral intensity (hereinafter sometimes referred to as "spin concentration") of the ESR spectrum is proportional to the concentration of isolated bivalent copper present in a sample. A high spin concentration means that a large amount of highly dispersed bivalent copper is contained, and the adsorption amount increases by an increase of the hydrocarbon adsorption sites.

Further, when a large amount of bivalent copper is contained, the thermal durability tends to be particularly high when the proportion of the peak intensity at a magnetic field of at least 260 mT and at most 270 mT to the peak intensity at a magnetic field of at least 300 mT and at most 320 mT is within a specific range. The peak at a magnetic field of at least 260 mT and at most 270 mT, and the peak at a magnetic field of at least 300 mT and at most 320 mT, respectively reflect the dispersed copper which interacts with D6R, and the whole dispersed copper species. Accordingly, the proportion of the peak intensity at a magnetic field of at least 260 mT and at most 270 mT to the peak intensity at a magnetic field of at least 300 mT and at most 320 mT is an index of the proportion of the dispersed copper which interacts with D6R present to the whole dispersed copper species.

The spin concentration is preferably at least $1.0 \times 10^{19}$ (spins/g), more preferably at least $1.5 \times 10^{19}$ (spins/g), further preferably at least $2.0 \times 10^{19}$ (spins/g).

The proportion of the peak intensity at a magnetic field of at least 260 mT and at most 270 mT to the peak intensity at a magnetic field of at least 300 mT and at most 320 mT is preferably at least 0.25 and at most 0.50, more preferably at least 0.30 and at most 0.45, further preferably at least 0.30 and at most 0.40.

The copper content in the FAU type zeolite is preferably at least 0.5 wt % and at most 4.0 wt %, more preferably at least 1.0 wt % and at most 3.0 wt %. In a specific embodiment, the copper content in the FAU type zeolite is preferably at least 1.5 wt % and at most 2.8 wt %. Further, in another embodiment, the copper content in the FAU type zeolite is preferably at least 1.0 wt % and at most 2.8 wt %, more preferably at least 1.0 wt % and at most 1.8 wt %.

In the embodiment of the present invention, the copper content in the FAU type zeolite is the weight ratio of copper to the weight of metals contained in the FAU type zeolite as calculated as oxides. For example, the copper content in a FAU type zeolite containing copper (Cu) and an alkali metal (M) can be obtained in accordance with the following formula.

$$\text{Copper content}(wt\%) = W'_{Cu}/(W_{Al} + W_{Si} + W_M + W_{Cu}) \times 100$$

wherein $W'_{Cu}$ is the copper (Cu) content, $W_{Al}$ is the weight of aluminum (Al) as calculated as oxide ($Al_2O_3$), $W_{Si}$ is the weight of silicon (Si) as calculated as oxide ($SiO_2$), $W_M$ is the weight of the alkali metal as calculated as oxide ($M_2O$), and $W_{Cu}$ is the weight of copper as calculated as oxide (CuO).

In the embodiment of the present invention, the FAU type zeolite may contain an alkali metal (that is, the alkali metal content may exceed 0 wt %), and the alkali metal content is preferably at most 1.0 wt %, whereby the hydrocarbon adsorbent according to the embodiment of the present invention tends to have high hydrocarbon adsorbing properties even after exposed to a high temperature/high humidity oxidizing atmosphere. The alkali metal content is preferably at least 0 wt % and at most 0.5 wt %, more preferably at least 0 wt % and at most 0.3 wt %, further preferably at least 0 wt % and at most 0.25 wt %.

In the embodiment of the present invention, the alkali metal contained in the FAU type zeolite may be at least either one of potassium (K) and sodium (Na), and particularly the alkali metal may be sodium.

In the embodiment of the present invention, the alkali metal content is the weight ratio of the alkali metal as calculated as oxide to the weight of the FAU type zeolite. Potassium and sodium as calculated as oxides are respectively potassium oxide ($K_2O$) and sodium oxide ($Na_2O$).

In the embodiment of the present invention, the average crystal size of the FAU type zeolite may be at least 0.1 μm, and is preferably at least 0.3 μm. The average crystal size of the FAU type zeolite is preferably at least 0.4 μm, more preferably at least 0.5 μm, whereby the hydrocarbon adsorbing properties after exposed not only to a reducing atmosphere but also to a high temperature/high humidity oxidizing atmosphere tend to be high.

With a view to improving workability such as coating property to the adsorbent carrier, the average crystal size of the FAU type zeolite is preferably at most 2.5 μm, more preferably at most 1.5 μm, further preferably at most 1.0 μm. In order that high hydrocarbon absorbing properties after exposed to a high temperature/high humidity atmosphere both in reducing atmosphere and in oxidizing atmosphere are obtained, the FAU type zeolite preferably has the above lattice constant and an average crystal size of at least 0.4 μm and at most 2.0 μm, particularly preferably at least 0.6 μm and at most 0.9 μm.

In the embodiment of the present invention, the average crystal size is the average particle size of primary particles. The particle size of a primary particle is a particle size of a primary particle confirmed in a scanning electron microscope (hereinafter sometimes referred to as "SEM") image obtained by SEM observation, and the average crystal size is the average of the particles sizes of primary particles. The method of measuring the average crystal size may be a method of selecting from 80 to 150 primary particles at random observed at 3,000 to 20,000 magnifications, measuring the particle sizes of the primary particles and taking the average as the average crystal size. To select the primary particles to measure the particle sizes, one or more SEM images may be employed.

In the embodiment of the present invention, the primary particles of the FAU type zeolite are particles observed as independent particles by SEM observation at 3,000 to 20,000 magnifications.

In the embodiment of the present invention, the FAU type zeolite has a BET specific surface area of preferably at least 500 $m^2/g$ and at most 900 $m^2/g$, more preferably at least 600 $m^2/g$ and at most 800 $m^2/g$.

In the embodiment of the present invention, the hydrocarbon adsorbent may contain a binding agent. The binding agent may be at least one selected from the group consisting of silica, alumina, kaolin, attapulgite, montmorillonite, bentonite, allophane and sepiolite.

In the embodiment of the present invention, the hydrocarbon adsorbent may be used for a method for adsorbing hydrocarbons, and is preferably used for a method for adsorbing hydrocarbons in an environment such that the hydrocarbon adsorbent is exposed to high temperature, more preferably used for a method for adsorbing hydrocarbons from an exhaust gas of an internal combustion engine, further preferably used for a method for adsorbing hydrocarbons from an exhaust gas of an internal combustion engine of a vehicle.

In the embodiment of the present invention, the hydrocarbon adsorbent may be used for a method for adsorbing hydrocarbons by a method comprising a step of bringing the hydrocarbon adsorbent into contact with a hydrocarbon-containing gas (hereinafter sometimes referred to as "contact step").

In the contact step, the shape of the hydrocarbon adsorbent is optional, and may be at least either one of a powder and a formed product.

In a case where the hydrocarbon absorbent is in the form of a powder, a slurry containing the hydrocarbon adsorbent may be applied to a substrate, which is used as an adsorbing member containing the adsorbent. In a case where the hydrocarbon adsorbent is in the form of a formed product, it may be used in an optional shape formed by an optional method, for example, at least one selected from the group consisting of tumbling granulation, press molding, extrusion, injection molding, casting and sheet forming. The shape of the formed product may be at least one selected from the group consisting of a sphere, a substantial sphere, an ellipse, a disk, a cylinder, a polyhedron, an indefinite shape and a petal.

The hydrocarbon-containing gas is a gas containing hydrocarbons, and the hydrocarbons may be at least either one of an aliphatic hydrocarbon and an aromatic hydrocarbon, preferably a $C_{6-15}$ hydrocarbon, more preferably an aromatic hydrocarbon, further preferably at least one selected from the group consisting of benzene, toluene and xylene.

The hydrocarbon concentration in the hydrocarbon-containing gas may be at least 0.001 vol % and at most 5 vol % as calculated as methane, preferably at least 0.005 vol % and at most 3 vol %. The hydrocarbon-containing gas may contain at least one selected from the group consisting of carbon monoxide, carbon dioxide, hydrogen, oxygen, nitrogen, nitrogen oxide, sulfur oxide and water.

In the contact step, conditions under which the hydrocarbon adsorbent and the hydrocarbon-containing gas are brought into contact with each other are optional. As the contact conditions, the following conditions may, for example, be mentioned.

Space velocity: at least 100 $hr^{-1}$ and at most 500,000 $hr^{-1}$
Contact adsorption: at least −30° C. and at most 200° C.

In the embodiment of the present invention, the hydrocarbon adsorbent may be produced by an optional method so long as copper is contained in the FAU type zeolite having a lattice constant of at least 24.29 Å.

In the embodiment of the present invention, as a method for producing the hydrocarbon adsorbent, a method for producing the hydrocarbon adsorbent may be mentioned, comprising a step of bringing a FAU type zeolite having a lattice constant of at least 24.29 Å and a copper source into contact with each other (hereinafter sometimes referred to as "metal contacting step") and a step of calcining the FAU type zeolite after the metal contacting step (hereinafter sometimes referred to as "calcining step").

In the metal contacting step, the lattice constant of the FAU type zeolite may sometimes change by contact with the copper source. Accordingly, the lattice constant of the FAU type zeolite to be subjected to the metal contacting step is preferably at least 24.29 Å and at most 24.60 Å, more preferably at least 24.29 Å and at most 24.57 Å.

The copper source is a compound containing copper (Cu), and is preferably a copper salt, more preferably at least one selected from the group consisting of a nitrate, sulfate, acetate, chloride, complex salt, oxide and composite oxide containing copper, further preferably at least one selected from the group consisting of copper nitrate, copper sulfate and copper acetate.

As the method of bringing the FAU type zeolite and the copper source into contact with each other, a known method may be employed, at least one selected from the group consisting of ion exchange method, impregnation method, evaporation-to-dryness method, precipitation method and physical mixing method may be mentioned, at least either one of ion exchange method an impregnation method is preferred, and impregnation method is more preferred.

After the FAU type zeolite and the copper source are brought into contact with each other, the FAU type zeolite may be washed and dried by an optional method. The washing method may be washing with a sufficient amount of water, and the drying method may be treatment in the air at from 100° C. to 150° C. for from 5 hours to 30 hours.

The calcining conditions in the calcining step are optional, and the following conditions may be mentioned.

| Calcining atmosphere: | in an oxidizing atmosphere, preferably in the air |
|---|---|
| Calcining temperature: | at least 400° C. and at most 600° C. |
| Calcining time: | at least 30 minutes and at most 5 hours |

The calcining step is carried out preferably in a stream of the air, and the air in the stream preferably has a low moisture content. By calcining in the air having a low moisture content, the interaction between copper and aluminum constituting the framework of the crystal structure tends to be strong, and the thermal durability tends to improve. The moisture content of the air in the stream is preferably at most 0.7 vol %, more preferably at most 0.5 vol %, further preferably at most 0.3 vol %.

EXAMPLES

Now, the present invention will be described in further detail with reference to Examples. However, it should be understood that the present invention is by no means restricted to such specific Examples. Reagents, etc. are commercial products unless otherwise specified.

(Average Crystal Size)

A sample was observed with a general scanning electron microscope (apparatus name: JSM-6390LV, manufactured by JEOL Ltd., hereinafter referred to as "SEM") under the following conditions to obtain SEM images of two fields of view each at magnifications of 5,000 and 15,000, i.e. 4 fields of view in total. 100 Primary particles were selected at random from the obtained SEM images, and the average value of the horizontal Feret's diameters was obtained and taken as the average crystal size.

(Compositional Analysis)

A sample was dissolved in a mixed aqueous solution of hydrofluoric acid and nitric acid to prepare a sample solution. The sample solution was measured by means of inductively coupled plasma atomic emission spectroscopy (ICP-AES) using a general ICP apparatus (apparatus name: OPTIMA5300DV, manufactured by PerkinElmer), and the composition was determined from the obtained measured values of the respective elements.

(Measurement of Hydrocarbon Adsorption Ratio)

The hydrocarbon adsorbent was pressure-formed, crushed and formed into agglomerated particles having an agglomerate size of from 20 to 30 mesh. 0.1 g of the agglomerated particles was filled in a normal pressure fixed bed flow reactor, treated in a stream of nitrogen at 500° C. for one hour and cooled to 50° C. to conduct pretreatment. A hydrocarbon-containing gas was made to flow through the hydrocarbon adsorbent after the pretreatment to measure the hydrocarbon adsorption ratio.

The composition of the hydrocarbon-containing gas and the conditions for the hydrocarbon adsorption measurement are shown below.

Hydrocarbon-containing gas: toluene 3,000 vol ppmC (concentration as calculated as methane)

| oxygen | 1 vol % |
|---|---|
| water | 3 vol % |
| nitrogen | the rest |
| Gas flow rate: | 200 mL/min |
| Temperature-raising rate: | 10° C./min |
| Measurement temperature: | 50 to 200° C. |
| Measurement time: | 15 minutes |

Using a flame ionization detector (FID), the hydrocarbons in the gas after made to flow through the hydrocarbon adsorbent were continuously quantitatively analyzed. The hydrocarbon concentration of the hydrocarbon-containing gas on the inlet side of the normal pressure fixed bed flow reactor (concentration as calculated as methane, hereinafter referred to as "inlet concentration") and the hydrocarbon concentration of the hydrocarbon-containing gas on the outlet side of the normal pressure fixed bed flow reactor (concentration as calculated as methane, hereinafter referred to as "outlet concentration") were measured.

The ratio of the integral value of the outlet concentration (concentration as calculated as methane) to the integral value of the inlet concentration was obtained as the hydrocarbon adsorption ratio.

(Reduction Hydrothermal Durability Treatment)

The hydrocarbon adsorbent was treated in the same manner as (measurement of hydrocarbon adsorption ratio) except that a treatment gas was made to flow through the hydrocarbon adsorbent after the pretreatment under the following conditions to conduct reduction hydrothermal durability treatment.

| Treatment gas: | propylene 3,000 vol ppmC (concentration calculated as methane) water 10 vol % nitrogen the rest |
|---|---|
| Gas flow rate: | 300 mL/min |
| Space velocity: | 6,000 hr$^{-1}$ |
| Treatment temperature: | 900° C. |
| Treatment time: | 2 hours |

(Oxidation Hydrothermal Durability Treatment)

The hydrocarbon adsorbent was treated in the same manner as (measurement of hydrocarbon adsorption ratio) except that a treatment gas was made to flow through the hydrocarbon adsorbent after the pretreatment under the following conditions to conduct oxidation hydrothermal durability treatment.

| Treatment gas: | water 10 vol % nitrogen the rest |
|---|---|
| Gas flow rate: | 300 mL/min |
| Space velocity: | 6,000 hr$^{-1}$ |
| Treatment temperature: | 900° C. |
| Treatment time: | 2 hours |

Example 1

10 g of a FAU type zeolite having a lattice constant of 24.53 Å and 4.58 g of an aqueous copper nitrate solution (containing 0.58 g of copper nitrate trihydrate) were mixed and dried in the air at 110° C. for overnight. The FAU type zeolite after drying was calcined in a stream of air having a moisture content of 0.1 vol % at 550° C. for 2 hours to obtain a copper-containing FAU type zeolite, which was taken as the hydrocarbon adsorbent in this Example.

The obtained copper-containing FAU type zeolite had a lattice constant of 24.49 Å, a $SiO_2/Al_2O_3$ ratio of 7.4, a copper content of 1.51 wt %, a sodium content of 0.09 wt % and an average crystal size of 0.81 μm.

Example 2

A copper-containing FAU type zeolite was obtained in the same manner as in Example 1 except that a FAU type zeolite having a lattice constant of 24.31 Å was used, which was taken as the hydrocarbon adsorbent in this Example.

The obtained copper-containing FAU type zeolite had a lattice constant of 24.31 Å, a $SiO_2/Al_2O_3$ ratio of 29.0, a copper content of 1.59 wt %, a sodium content of 0.12 wt % and an average crystal size of 0.71 μm.

Example 3

A copper-containing FAU type zeolite was obtained in the same manner as in Example 1 except that a FAU type zeolite having a lattice constant of 24.52 Å was used and that 4.98 g of an aqueous copper nitrate solution (containing 0.98 g of copper nitrate trihydrate) was used, which was taken as the hydrocarbon adsorbent in this Example.

The obtained copper-containing FAU type zeolite had a lattice constant of 24.48 Å, a $SiO_2/Al_2O_3$ ratio of 7.1, a copper content of 2.62 wt %, a sodium content of 0.09 wt % and an average crystal size of 0.75 μm.

Example 4

A copper-containing FAU type zeolite was obtained in the same manner as in Example 1 except that a FAU type zeolite having a lattice constant of 24.52 Å was used and that 4.38 g of an aqueous copper nitrate solution (containing 0.38 g of copper nitrate trihydrate) was used, which was taken as the hydrocarbon adsorbent in this Example.

The obtained copper-containing FAU type zeolite had a lattice constant of 24.47 Å, a $SiO_2/Al_2O_3$ ratio of 7.1, a copper content of 1.02 wt %, a sodium content of 0.09 wt % and an average crystal size of 0.75 μm.

Example 5

A copper-containing FAU type zeolite was obtained in the same manner as in Example 1 except that 5.16 g of an aqueous copper nitrate solution (containing 1.16 g of copper nitrate trihydrate) was used, which was taken as the hydrocarbon adsorbent in this Example.

The obtained copper-containing zeolite had a lattice constant of 24.49 Å, a $SiO_2/Al_2O_3$ ratio of 7.4, a copper content of 2.99 wt %, a sodium content of 0.09 wt % and an average crystal size of 0.81 μm.

Example 6

A copper-containing FAU type zeolite was obtained in the same manner as in Example 1 except that a FAU type zeolite having a lattice constant of 24.48 Å was used, which was taken as the hydrocarbon adsorbent in this Example.

The obtained copper-containing FAU type zeolite had a lattice constant of 24.43 Å, a $SiO_2/Al_2O_3$ ratio of 6.1, a copper content of 1.56 wt %, a sodium content of 0.24 wt % and an average crystal size of 0.75 μm.

Example 7

A copper-containing FAU type zeolite was obtained in the same manner as in Example 1 except that a FAU type zeolite having a lattice constant of 24.48 Å was used, which was taken as the hydrocarbon adsorbent in this Example.

The obtained copper-containing FAU type zeolite had a lattice constant of 24.46 Å, a $SiO_2/Al_2O_3$ ratio of 5.4, a copper content of 1.59 wt %, a sodium content of 4.02 wt % and an average crystal size of 0.36 μm.

Example 8

A copper-containing FAU type zeolite was obtained in the same manner as in Example 1 except that a FAU type zeolite having a lattice constant of 24.37 Å was used, which was taken as the hydrocarbon adsorbent in this Example.

The obtained copper-containing FAU type zeolite had a lattice constant of 24.34 Å, a $SiO_2/Al_2O_3$ ratio of 6.0, a copper content of 1.59 wt %, a sodium content of 0.30 wt % and an average crystal size of 0.36 μm.

Example 9

50 g of a FAU type zeolite having a lattice constant of 24.63 Å was ion-exchanged with 125 g of an aqueous 20% ammonium chloride solution, washed with 1 L of pure water and dried at 110° C. overnight. The dried powder was calcined in a 60 vol % water-containing air at 600° C. for 4 hours. 20 g of the calcined powder was put into 100 g of 1.6% hydrochloric acid and subjected to heat treatment at 60° C. for one hour. Then, the powder was washed with 1 L of pure water and further ion-exchanged with 600 g of 20% ammonium chloride and washed with 1 L of pure water to obtain a FAU type zeolite of 24.55 Å.

A copper-containing FAU type zeolite was obtained in the same manner as in Example 3 except that the above FAU type zeolite was used, which was taken as the hydrocarbon adsorbent in this Example.

The obtained copper-containing FAU type zeolite had a lattice constant of 24.51 Å, a $SiO_2/Al_2O_3$ ratio of 7.0, a copper content of 2.51 wt %, a sodium content of 0.29 wt % and an average crystal size of 0.75 μm.

Example 10

50 g of a FAU type zeolite having a lattice constant of 24.63 Å was ion-exchanged with 125 g of an aqueous 10% ammonium chloride solution, washed with 1 L of pure water and dried at 110° C. overnight. The dried powder was calcined in a 60 vol % water-containing air at 740° C. for 2 hours. 20 g of the calcined powder was put into 100 g of 1.6% hydrochloric acid and subjected to heat treatment at 60° C. for one hour. Then, the powder was washed with 1 L of pure water to obtain a FAU type zeolite of 24.50 Å.

A copper-containing FAU type zeolite was obtained in the same manner as in Example 3 except that the above FAU type zeolite was used, which was taken as the hydrocarbon adsorbent in this Example.

The obtained copper-containing FAU type zeolite had a lattice constant of 24.48 Å, a $SiO_2/Al_2O_3$ ratio of 6.1, a copper content of 2.47 wt %, a sodium content of 0.73 wt % and an average crystal size of 0.75 μm.

Example 11

50 g of a FAU type zeolite having a lattice constant of 24.63 Å was ion-exchanged with 50 g of an aqueous 10% ammonium chloride solution, washed with 1 L of pure water and dried at 110° C. overnight. The dried powder was calcined in a 60 vol % water-containing air at 600° C. for 4 hours. 20 g of the calcined powder was put into 100 g of 1.6% hydrochloric acid and subjected to heat treatment at 60° C. for one hour. Then, the powder was washed with 1 L of pure water and further ion-exchanged with 600 g of 20% ammonium chloride and washed with 1 L of pure water to obtain a FAU type zeolite of 24.60 Å.

A copper-containing FAU type zeolite was obtained in the same manner as in Example 1 except that the above FAU type zeolite was used, and that 4.98 g of an aqueous copper nitrate solution (containing 0.98 g of copper nitrate trihydrate) was used, which was taken as the hydrocarbon adsorbent in this Example.

The obtained copper-containing FAU type zeolite had a lattice constant of 24.52 Å, a $SiO_2/Al_2O_3$ ratio of 7.1, a copper content of 2.50 wt %, a sodium content of 0.57 wt % and an average crystal size of 0.75 µm.

Example 12

A copper-containing FAU type zeolite was obtained in the same manner as in Example 1 except that a FAU type zeolite having a lattice constant of 24.52 Å was used and that 6.00 g of an aqueous copper nitrate solution (containing 2.00 g of copper nitrate trihydrate) was used, which was taken as the hydrocarbon adsorbent in this Example.

The obtained copper-containing FAU type zeolite had a lattice constant of 24.50 Å, a $SiO_2/Al_2O_3$ ratio of 7.1, a copper content of 4.73 wt %, a sodium content of 0.09 wt % and an average crystal size of 0.75 µm.

Comparative Example 1

A FAU type zeolite having a lattice constant of 24.53 Å was used as the hydrocarbon adsorbent in this Comparative Example. The copper-containing FAU type zeolite had a lattice constant of 24.53 Å, a $SiO_2/Al_2O_3$ ratio of 7.4, a copper content of 0 wt %, a sodium content of 0.09 wt % and an average crystal size of 0.81 µm.

Comparative Example 2

A copper-containing FAU type zeolite was obtained in the same manner as in Example 1 except that a FAU type zeolite having a lattice constant of 24.25 Å was used, which was taken as the hydrocarbon adsorbent in this Comparative Example.

The obtained copper-containing FAU type zeolite had a lattice constant of 24.25 Å, a $SiO_2/Al_2O_3$ ratio of 14.9, a copper content of 1.57 wt %, a sodium content being the detection limit or lower and an average crystal size of 0.38 µm.

Comparative Example 3

A copper-containing FAU type zeolite was obtained in the same manner as in Example 1 except that a FAU type zeolite having a lattice constant of 24.28 Å was used, which was taken as the hydrocarbon adsorbent in this Comparative Example.

The obtained copper-containing FAU type zeolite had a lattice constant of 24.27 Å, a $SiO_2/Al_2O_3$ ratio of 28.0, a copper content of 1.60 wt %, a sodium content of 0.10 wt % and an average crystal size of 0.60 µm.

Comparative Example 4

A copper-containing MFI type zeolite was obtained in the same manner as in Example 1 except that a MFI type zeolite was used and that 4.58 g of an aqueous copper nitrate solution (containing 0.58 g of copper nitrate trihydrate) was used, which was taken as the hydrocarbon adsorbent in this Comparative Example.

The obtained copper-containing MFI type zeolite had a $SiO_2/Al_2O_3$ ratio of 38, a copper content of 1.52 wt % and a sodium content of 0.02 wt %.

Comparative Example 5

A copper-containing BEA type zeolite was obtained in the same manner as in Example 1 except that a BEA type zeolite was used and that 4.58 g of an aqueous copper nitrate solution (containing 0.58 g of copper nitrate trihydrate) was used, which was taken as the hydrocarbon adsorbent in this Comparative Example.

The obtained copper-containing BEA type zeolite had a $SiO_2/Al_2O_3$ ratio of 40, a copper content of 1.47 wt % and a sodium content of 0.04 wt %.

Comparative Example 6

15 g of a MFI type zeolite was added to 135 g of an aqueous silver nitrate solution (silver nitrate concentration: 3.2 wt %) followed by mixing with stirring at 60° C. overnight to ion-exchange the zeolite. The ion-exchanged MFI type zeolite was subjected to filtration, washed and dried in the air at 110° C. overnight to obtain a silver-containing MFI type zeolite, which was taken as the hydrocarbon adsorbent in this Comparative Example.

The obtained silver-containing MFI type zeolite had a $SiO_2/Al_2O_3$ ratio of 38.0, a silver content of 4.50 wt % and a sodium content being the detection limit or lower.

Comparative Example 7

A copper-containing FAU type zeolite was obtained in the same manner as in Example 1 except that a FAU type zeolite having a lattice constant of 24.26 Å was used and that 4.98 g of an aqueous copper nitrate solution (containing 0.98 g of copper nitrate trihydrate) was used, which was taken as the hydrocarbon adsorbent in this Example.

The obtained copper-containing FAU type zeolite had a lattice constant of 24.26 Å, a $SiO_2/Al_2O_3$ ratio of 103, a copper content of 2.53 wt %, a sodium content of 0.09 wt % and an average crystal size of 0.77 µm.

Measurement Example 1

The hydrocarbon adsorbent in each of Examples 1 and 2 and Comparative Examples 1 to 3 was subjected to reduction hydrothermal durability treatment. The hydrocarbon adsorption ratio of each hydrocarbon adsorbent after the reduction hydrothermal durability treatment was measured. The results are shown in the following Table.

TABLE 1

| | Lattice constant (Å) | SiO$_2$/Al$_2$O$_3$ ratio | Copper content (wt %) | Hydrocarbon adsorption ratio (%) |
|---|---|---|---|---|
| Example 1 | 24.49 | 7.4 | 1.51 | 46 |
| Example 2 | 24.31 | 29.0 | 1.59 | 46 |
| Comparative Example 1 | 24.52 | 7.4 | 0 | 3 |
| Comparative Example 2 | 24.25 | 14.9 | 1.57 | 11 |
| Comparative Example 3 | 24.28 | 28.0 | 1.60 | 17 |

It was confirmed from Example 1 and Comparative Example 1 that the hydrocarbon adsorption ratio of the hydrocarbon adsorbent containing no copper is remarkably low.

The hydrocarbon adsorbents in Examples 1 and 2 and Comparative Examples 2 and 3 contain copper at the same level. However, it is confirmed that the hydrocarbon adsorbents in Examples 1 and 2 with a lattice constant of at least 24.31 Å have a remarkably high hydrocarbon adsorption ratio as compared with the hydrocarbon adsorbents in Comparative Examples 2 and 3 with a lattice constant of less than 24.29 Å.

Figure 2:
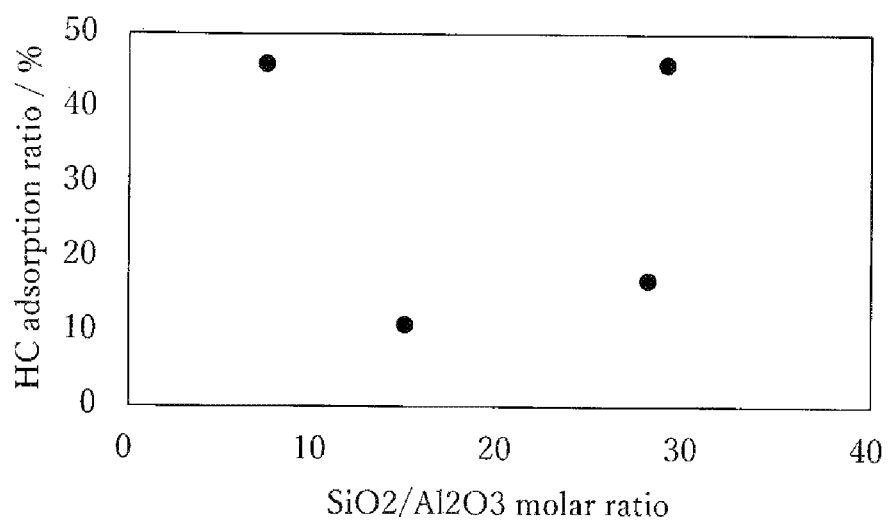
FIG. 2 is a graph illustrating the relation between the $SiO_2/Al_2O_3$ molar ratio and the hydrocarbon adsorption ratio after reduction hydrothermal durability treatment.

Of the hydrocarbon adsorbents containing copper, the relation between the lattice constant and the hydrocarbon adsorption ratio is shown in FIG. 1, and the relation between the SiO$_2$/Al$_2$O$_3$ ratio and the hydrocarbon adsorption ratio is shown in FIG. 2. It is confirmed from FIG. 1 that the hydrocarbon adsorption ratio is remarkably high when the lattice constant is at least 24.29 Å. Further, no correlation between the SiO$_2$/Al$_2$O$_3$ ratio and the hydrocarbon adsorption ratio is confirmed from FIG. 2.

Measurement Example 2

Figure 3:
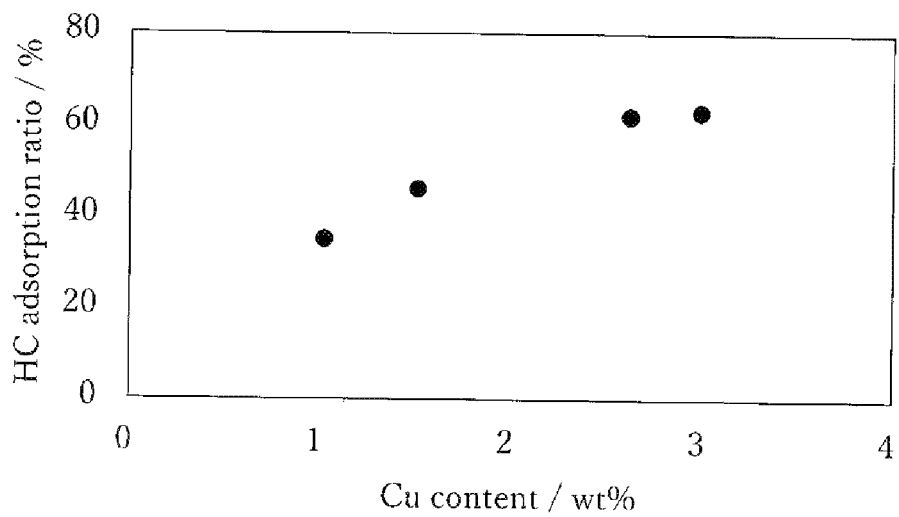
FIG. 3 is a graph illustrating the relation between the copper content and the hydrocarbon adsorption ratio after reduction hydrothermal durability treatment.

The hydrocarbon adsorbent in each of Examples 3 to 5 and 12 was subjected to reduction hydrothermal durability treatment. The hydrocarbon adsorption ratio of each hydrocarbon adsorbent after the reduction hydrothermal durability treatment was measured. The results are shown in the following Table and FIG. 3 together with the results in Example 1 in Measurement Example 1.

TABLE 2

| | Lattice constant (Å) | SiO$_2$/Al$_2$O$_3$ ratio | Copper content (wt %) | Hydrocarbon adsorption ratio (%) |
|---|---|---|---|---|
| Example 1 | 24.49 | 7.4 | 1.51 | 46 |
| Example 3 | 24.48 | 7.1 | 2.62 | 62 |
| Example 4 | 24.47 | 7.1 | 1.09 | 32 |
| Example 5 | 24.49 | 7.4 | 2.99 | 63 |
| Example 12 | 24.50 | 7.1 | 4.73 | 82 |

It is confirmed from this Measurement Example that the hydrocarbon adsorption ratio after the reduction hydrothermal durability treatment tends to be high as the copper content increases.

Measurement Example 3

The hydrocarbon adsorbent in each of Examples 6 to 8 was subjected to reduction hydrothermal durability treatment. The hydrocarbon adsorption ratio of each hydrocarbon adsorbent after the reduction hydrothermal durability treatment was measured. The results are shown in the following Table together with the results in Comparative Example 3 in Measurement Example 1.

TABLE 3

| | Lattice constant (Å) | Copper content (wt %) | Average crystal size (μm) | Sodium content (wt %) | Hydrocarbon adsorption ratio (%) |
|---|---|---|---|---|---|
| Example 6 | 24.43 | 1.56 | 0.75 | 0.24 | 47 |
| Example 7 | 24.46 | 1.59 | 0.36 | 4.02 | 32 |
| Example 8 | 24.34 | 1.59 | 0.36 | 0.30 | 42 |
| Comparative Example 3 | 24.28 | 1.60 | 0.60 | 0.10 | 17 |

It is confirmed from this Measurement Example that the hydrocarbon adsorption ratio tends to decrease as the average crystal size becomes smaller and as the sodium content increases. However, it is confirmed that the hydrocarbon adsorbent in each Example has a high hydrocarbon adsorption ratio as compared with the hydrocarbon adsorbent in Comparative Example 3 with a lattice constant of less than 24.29 Å.

Measurement Example 4

The hydrocarbon adsorbent in each of Comparative Examples 4 to 6 was subjected to reduction hydrothermal durability treatment. The hydrocarbon adsorption ratio of each hydrocarbon adsorbent after the reduction hydrothermal durability treatment was measured. The results are shown in the following Table together with the results in Example 4 in Measurement Example 1.

TABLE 4

| | Crystal structure (Å) | Metal species contained | Metal content (wt %) | Hydrocarbon adsorption ratio (%) |
|---|---|---|---|---|
| Example 4 | FAU | Cu | 1.02 | 35 |
| Comparative Example 4 | MFI | Cu | 1.52 | 0 |
| Comparative Example 5 | BEA | Cu | 1.47 | 8 |
| Comparative Example 6 | MFI | Ag | 4.50 | 13 |

It is confirmed that the hydrocarbon adsorbent in Example 4 has a remarkably high hydrocarbon adsorption ratio although it has a low metal content, as compared with the BEA type zeolite and the MFI type zeolite which have been used as conventional hydrocarbon adsorbents.

Measurement Example 5

The hydrocarbon adsorbent in each of Examples 1, 2, 3, 6 and 8 and Comparative Examples 3 and 6 was subjected to oxidation hydrothermal durability treatment. The hydrocarbon adsorption ratio of each hydrocarbon adsorbent after the oxidation hydrothermal durability treatment was measured. The results are shown in the following Table.

TABLE 5

| | Lattice constant (Å) | Metal species contained | Metal content (wt %) | Average crystal size (μm) | Hydrocarbon adsorption ratio (%) |
|---|---|---|---|---|---|
| Example 1 | 24.49 | Cu | 1.51 | 0.81 | 47 |
| Example 2 | 24.31 | Cu | 1.59 | 0.71 | 32 |
| Example 3 | 24.48 | Cu | 2.62 | 0.75 | 60 |
| Example 6 | 24.43 | Cu | 1.56 | 0.75 | 37 |
| Example 8 | 24.34 | Cu | 1.59 | 0.36 | 18 |
| Comparative Example 3 | 24.28 | Cu | 1.60 | 0.60 | 9 |
| Comparative Example 6 | — | Ag | 4.50 | — | 26 |

It is confirmed from this Measurement Example that regarding the hydrocarbon adsorbents containing copper, the hydrocarbon adsorbent having a lattice constant of at least 24.29 Å has a high hydrocarbon adsorption ratio after the oxidation hydrothermal durability treatment as compared with the hydrocarbon adsorbent having a lattice constant of less than 24.29 Å. Further, it is confirmed from Example 8 and Comparative Example 3 that the hydrocarbon adsorbent having a lattice constant of at least 24.29 Å, even having a small average particle size, has a high hydrocarbon adsorption ratio after the oxidation hydrothermal durability treatment as compared with the FAU type zeolite having a lattice constant of less than 24.29 Å.

Further, it is confirmed that even as compared with the conventional hydrocarbon adsorbent in Comparative Example 6, the hydrocarbon adsorbent having a larger average crystal size than the hydrocarbon adsorbent in Example 8 has a high hydrocarbon adsorption ratio after the oxidation hydrothermal durability treatment.

Measurement Example 6

The hydrocarbon adsorbent in each of Examples 9, 10 and 11 was subjected to oxidation hydrothermal durability treatment. The hydrocarbon adsorption ratio of each hydrocarbon adsorbent after the oxidation hydrothermal durability treatment was measured. The results are shown in the following Table.

TABLE 6

| | Lattice constant (Å) | Copper content (wt %) | Average crystal size (μm) | Sodium content (wt %) | Hydrocarbon adsorption ratio (%) |
|---|---|---|---|---|---|
| Example 9 | 24.51 | 2.51 | 0.75 | 0.29 | 43 |
| Example 10 | 24.48 | 2.47 | 0.75 | 0.73 | 45 |
| Example 11 | 24.52 | 2.50 | 0.71 | 0.57 | 0 |

It is confirmed from Examples 9 and 11 in this Measurement Example that the hydrocarbon adsorbent having a lattice constant of at most 24.51 Å has a high hydrocarbon adsorption ratio after the oxidation hydrothermal durability treatment.

Measurement Example 7

The hydrocarbon adsorbent in each of Example 1 and Comparative Example 3 was pressure-formed, crushed and formed into agglomerated particles having an agglomerated size of from 12 to 20 mesh. 0.3 g of each of the agglomerated particles was weighed, subjected to high temperature reduction treatment and then subjected to high temperature oxidation treatment. The conditions for the high temperature reduction treatment and the high temperature oxidation treatment are as follows.

| High temperature reduction treatment: | |
|---|---|
| treatment atmosphere | 5 vol % hydrogen-containing helium atmosphere |
| treatment temperature | 900° C. |
| treatment time | 0.5 hour |
| High temperature oxidation treatment: | |
| treatment atmosphere | air atmosphere |
| treatment temperature | 500° C. |
| treatment time | 1 hour |

Each hydrocarbon adsorbent after the treatments was subjected to pretreatment and then subjected to $H_2$-TPR measurement. The pretreatment and $H_2$-TPR conditions are shown below, the results in Example 1 are shown in FIG. 4, and the results in Comparative Example 3 are shown in FIG. 5.

| Pretreatment: | atmosphere | helium atmosphere |
|---|---|---|
| | treatment temperature | 300° C. |
| | treatment time | 0.5 hour |
| $H_2$-TPR: | atmosphere | 5 vol % hydrogen-containing air |
| | temperature-raising rate | 10° C./hr |
| | measurement temperature | 100° C. to 700° C. |

Figure 4:
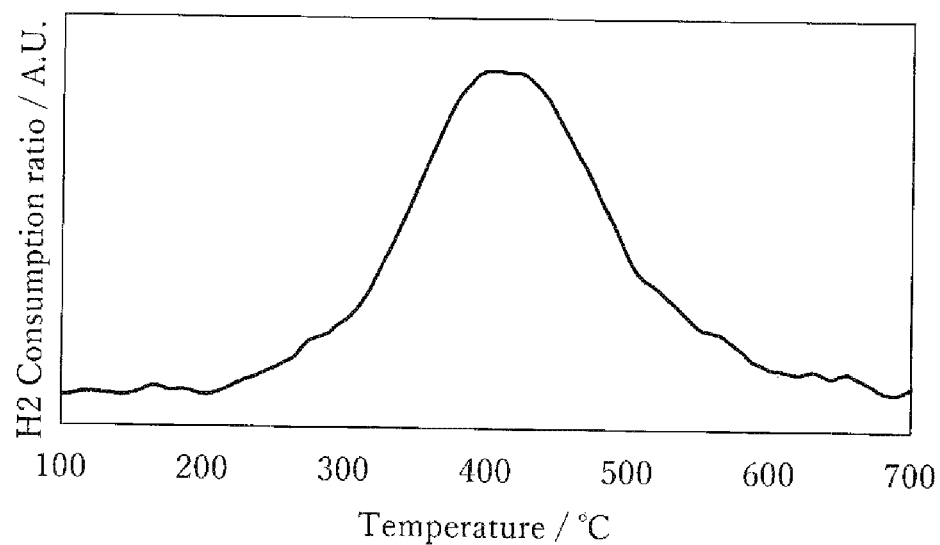
FIG. 4 illustrates $H_2$-TPR measurement results of Example 1.
Figure 5:
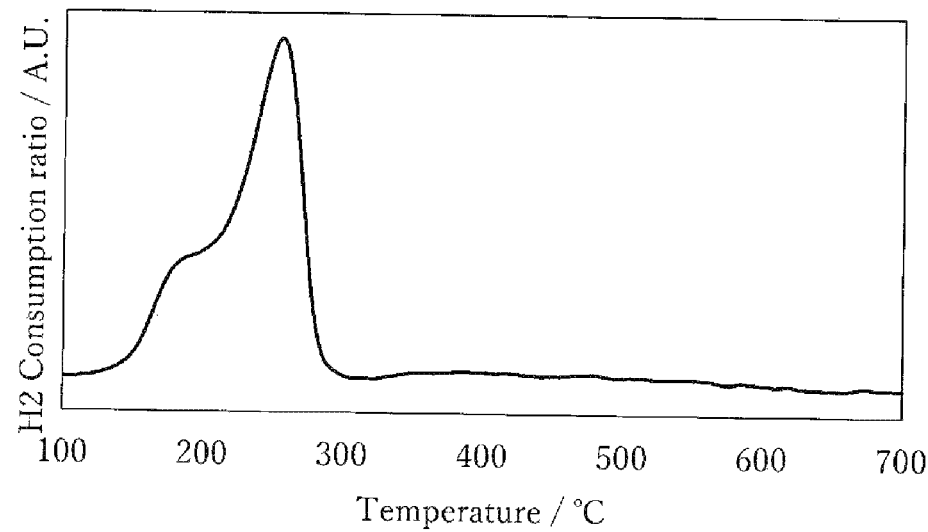
FIG. 5 illustrates $H_2$-TPR measurement results of Comparative Example 3.

From FIGS. 4 and 5, a hydrogen consumption peak with a peak top in the vicinity of 400° C. is confirmed for the hydrocarbon absorbent in Example 1 after subjected to the high temperature reduction treatment and the high temperature oxidation treatment, whereas no hydrogen consumption peak with a peak top at 300° C. or higher was confirmed for the hydrocarbon adsorbent in Comparative Example 3.

Measurement Example 8

The hydrocarbon adsorbent in each of Examples 1, 3, 5 and 12 and Comparative Example 7 was subjected to ESR measurement under the following conditions.

| Measurement apparatus: | manufactured by JEOL Ltd., JES-TE200 |
|---|---|
| Microwave frequency: | 9.4 GHz |
| Measurement range: | 200 to 400 mT |
| Magnetic field modulation: | 100 KHz |
| Response: | 0.3 sec. |
| Magnetic field sweep time: | 4 min. |
| Microwave output: | 1.0 mW |

As a sample (hydrocarbon adsorbent), 10 mg of a powder was filled in a quartz tube having a diameter of 5 mm and dried at 400° C. for 5 hours, and the tube was sealed.

Figure 6:
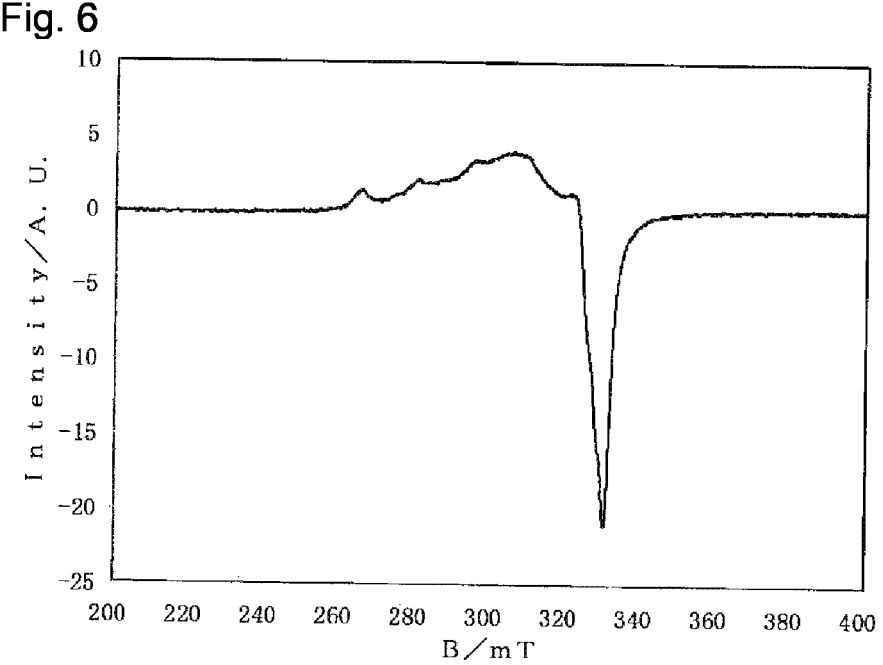
FIG. 6 illustrates ESR measurement results of Example 3.

The ESR spectrum of Example 3 obtained by the ESR measurement is shown in FIG. 6.

The spin concentration was obtained by double integration at a magnetic field within a range of from 220 to 380 mT by analysis software ES-IPRITS DATA SYSTEM version 6.2.

From the obtained ESR spectrum, the ratio of the peak intensity at a magnetic field at least 260 mT and at most 270 mT to the peak intensity at a magnetic field of at least 300 mT and at most 320 mT was calculated. In the following, the peak at a magnetic field of at least 260 mT and at most 270 mT will sometimes be referred to as "peak 1", the peak at a magnetic field of at least 300 mT and at most 320 mT as "peak 2", and the ratio of the peak intensity at a magnetic field of at least 260 mT and at most 270 mT to the peak intensity at a magnetic field of at least 300 mT and at most 320 mT as "peak 1/peak 2 intensity ratio".

TABLE 7

|  | Copper content (wt %) | Spin concentration (spin/g) | Peak 1/ peak 2 intensity ratio | Hydrocarbon adsorption ratio after hydrothermal durability treatment (%) |
| --- | --- | --- | --- | --- |
| Example 1 | 1.51 | $9.2 \times 10^{19}$ | 0.42 | 43 |
| Example 3 | 2.62 | $1.1 \times 10^{20}$ | 0.35 | 60 |
| Example 5 | 2.99 | $2.1 \times 10^{19}$ | 0.26 | 23 |
| Example 12 | 4.73 | $4.6 \times 10^{20}$ | 0.10 | 0 |
| Comparative Example 7 | 2.50 | $1.2 \times 10^{18}$ | Peak 1 not confirmed | 0 |

From comparison between Examples 1, 3 and 5, and Example 12 and Comparative Example 7, in this Measurement Example, the hydrocarbon adsorption ratio after the oxidation hydrothermal durability treatment is high when the spin concentration is at least $1.0 \times 10^{19}$ (spins/g) and the peak 1/peak 2 intensity ratio is at least 0.25 and at most 0.50.

The present invention has been described in detail with reference to specific embodiments, but, it is obvious for the person skilled in the art that various changes and modifications are possible without departing from the intention and the scope of the present invention.

The entire disclosure of Japanese Patent Application No. 2018-037603 filed on Mar. 2, 2018 including specification, claims, drawings and summary is incorporated herein by reference in its entirety.

INDUSTRIAL APPLICABILITY

The hydrocarbon adsorbent of the present invention may be used for a method for adsorbing hydrocarbons to be exposed to a high temperature/high humidity environment, and may be used particularly for a method for adsorbing hydrocarbons in an exhaust gas in an internal combustion engine, such as an automobile exhaust gas.

What is claimed is:

1. A hydrocarbon adsorbent, which comprises FAU type zeolite containing bivalent copper having, in ESR measurement a spin concentration of a least $1.0 \times 10^{19}$ (spins/g) and a ratio of a peak intensity at a magnetic field of at least 260 mT and at most 270 mT to a peak intensity at a magnetic field of at least 300 mT and at most 320 mT of at least and at most 0.50.

2. The hydrocarbon adsorbent according to claim 1, wherein the FAU type zeolite has an average crystal size of at least 0.45 μm.

3. The hydrocarbon adsorbent according to claim 1, wherein the FAU type zeolite has a copper content of at least 0.5 wt % and at most 4.0 wt %.

4. The hydrocarbon adsorbent according to claim 1, wherein the FAU type zeolite has an alkali metal content as calculated as oxides of at most 1 wt %.

5. The hydrocarbon adsorbent according to claim 1, wherein the FAU type zeolite has a hydrogen consumption peak with a peak top at a temperature of at least 300° C. and at most 500° C., in $H_2$-TRP measurement in a state after subjected to exposure treatment to a reducing atmosphere at a temperature of at least 800° C. and at most 1,000° C. and then to exposure treatment to an oxidizing atmosphere at a temperature of at least 400° C. and at most 600° C.

6. A method for treating a hydrocarbon-containing gas comprising contacting the hydrocarbon-contain gas with the hydrocarbon adsorbent as defined in claim 1.

\* \* \* \* \*

UNITED STATES PATENT AND TRADEMARK OFFICE
CERTIFICATE OF CORRECTION

PATENT NO. : 11,911,742 B2
APPLICATION NO. : 18/130577
DATED : February 27, 2024
INVENTOR(S) : K. Nakao et al.

It is certified that error appears in the above-identified patent and that said Letters Patent is hereby corrected as shown below:

In the Claims

Column 20, Line 15 (Claim 1, Line 6) please change "least and" to -- least 0.25 and --

Signed and Sealed this
Third Day of September, 2024

Katherine Kelly Vidal
*Director of the United States Patent and Trademark Office*